United States Patent
Burchell et al.

(12) 
(10) Patent No.: US 6,331,395 B1
(45) Date of Patent: Dec. 18, 2001

(54) PRENATAL DIAGNOSTIC METHODS

(75) Inventors: Ann Burchell, Tayport; Robert Hume, Dundee, both of (GB)

(73) Assignee: The University of Dundee (GB)

( * ) Notice: Subject to any disclaimer, the term of this patent is extended or adjusted under 35 U.S.C. 154(b) by 0 days.

(21) Appl. No.: 09/392,055

(22) Filed: Sep. 8, 1999

Related U.S. Application Data

(63) Continuation of application No. PCT/GB98/00656, filed on Mar. 3, 1998.
(60) Provisional application No. 60/067,520, filed on Dec. 4, 1997.

(30) Foreign Application Priority Data

Mar. 8, 1997 (GB) .................................................. 9704876

(51) Int. Cl.⁷ ........................ G01N 33/573; G01N 33/68; G01N 33/569; G01N 33/80
(52) U.S. Cl. ......................... 435/6; 435/2; 435/4; 435/5; 435/7; 435/7.21; 435/320.1; 435/194; 435/196; 435/7.1; 435/252.3; 435/240.1; 435/975; 435/810; 435/91.2; 435/7.24; 435/7.25; 435/40.5; 435/7.5; 435/7.72; 435/7.9; 435/7.92; 436/63; 436/519; 436/520; 436/524; 436/510; 436/518; 436/527; 436/66; 436/80; 935/77
(58) Field of Search .................................... 435/2, 4, 5, 6, 435/7, 7.21, 320.1, 194, 196, 7.1, 252.3, 240.1, 975, 810, 91.2, 7.24, 7.25, 40.5, 7.5, 7.72, 7.9, 7.92; 436/63, 519, 520, 524, 510, 518, 527, 66, 800; 530/350, 389.6, 388.7; 536/23.2, 24.31, 24.3, 25.4; 935/77, 78

(56) References Cited

U.S. PATENT DOCUMENTS 5,460,942 * 10/1995 Chou et al. .............................. 435/6
5,641,628 * 11/1994 Bianchi .................................... 435/6
5,714,325 * 9/1993 Bianchi .................................... 435/6
5,731,156 * 10/1996 Golbus .................................. 435/7.1
5,859,699  1/1999 Baer et al. ........................... 356/246

FOREIGN PATENT DOCUMENTS 9107660   5/1991  (WO) .
9114768   10/1991 (WO) .
WO 93/23754 * 11/1993 (WO) .......................... G01N/33/543
9609409   3/1996  (WO) .

OTHER PUBLICATIONS

Lavabre–Bertrand et al., Quantification of CD24 and CD45 Antigen in parallel allows a precise determination of B–cell maturation stages . . . , Leukemia, vol. 8, No. 3, Mar. 1994, pp. 402–408.*

Spector et al., "Properties of fetal and adult red blood cell arginase: A possible prenatal diagnostic test for arginase deficiency.", Am j Hum Genet., vol. 32, pp. 79–87, 1980.*

(List continued on next page.)

*Primary Examiner*—Christopher L. Chin
*Assistant Examiner*—Lisa V. Cook
(74) *Attorney, Agent, or Firm*—Oppenheimer Wolff & Donnelly LLP; Michael B. Farber

(57) ABSTRACT

A method of identifying embryonic or fetal red blood cells in a sample containiing maternal blood cells and embryonic or fetal red blood cells or both, the method comprising determining which cell or cells contain or express an adult liver component. A method of isolating embryonic or fetal red blood cells from a sample containing maternal blood cells and embryonic or fetal red blood cells or both, the method comprising isolating the cells which contain or express an adult liver component. A method of determining a fetal abnormality the method comprising identifying or isolating embryonic or fetal cells according to the above methods and analysing said embryonic or early fetal cells for said abnormality. Use of a means for determining whether a cell contains or expresses an adult liver component for identifying or isolating an embryonic or fetal red blood cell.

1 Claim, 1 Drawing Sheet

OTHER PUBLICATIONS

Acta Histochem. Jena (98, 29–37 (1996) A Rapid Combined Immunocytochemical and Fluorescence in Situ Hybridisation Method for the Identification of Human Fetal Nucleated Red Blood Cells, Sima Pazouki, Robert Hume, and Ann Burchell.

Vol. 4, Issue 1, Report on the Sixth Fetal Cell Workshop Held in Nottingham on Thursday, Dec. 5$^{th}$, 1996, David Liu and Lindy Durrant.

News & Views, Nature Genetics, vol. 14, Nov. 1996, Towards Non–Invasive Prenatal Diagnosis, Bob Williamson, p. 239–240.

JAMA, Nov. 17, 1993, vol. 270, No. 19, Isolating Fetal Cells From Maternal Blood, Simpson and Elias 2357–2361.

J. Clin. Pathol 1992;45 (Supplement): 39–45, Glucose Metabolism and Hypoglycaemia in SIDS, A. Burchell, H. Lyall, A. Busuttil, E. Bell, and R. Hume.

Journal of Immunological Methods, 131 (1990) 147–149, One Step Separation of Human Fetal Lymphocytes from Nucleated Red Blood Cells, Neelima M. Bhat, Marcia M. Bieber, and Nelson N. H. Teng.

Biochem. J. (1991) 275, 133–137, Transverse Topology of Glucose–6–Phosphatase in Rat Hepatic Endoplastic Reticulum, Ian D. Waddell and Ann Burchell.

Clin. Chem. 33/10. 1793–1787 (1987), Alkaline Phosphatase Isoenzymes in the Plasma of Preterm and Term Infants: Serial Measurements and Clinical Correlations, Patricia M. Crofton and Robert Hume.

The Lancet, Oct. 13, 1984, Trophoblast Cells in Peripheral Blood From Pregnant Women, p. 841–843, A. E. Covone, P. M. Johnson, D. Mutton, and M. Adinofli.

Prenatal Diagnosis With Fetal Cells Isolated From Maternal Blood by Multiparameter Flow Cytometry, James O. Price, Sherman Elias, Stephen S. Wachtel, Katherine Klinger, Michael Dockter, Avirachan Tharapel, Lee P. Shulman, Owen P. Philips, Carole M. Meyers, Donna Shook, and Joe Leigh Simpson, p. 1731–1735.

Nature, May 30, 1964, vol. 202, p. 910–911.

Prenatal Diagnosis, vol. 8, 401–404 (1988) The Prenatal Determination of Glucose–6–Phosphatase Activity by Fetal Liver Biopsy.

Seminars in Perinatology, vol. 14, No. 6 (Dec.), 1990: pp. 471–482, Prenatal Diagnosis Using Fetal Cells in the Material Circulation, Jane Chueh and Mitchell S. Globus.

Proc. Natl. Acad. Sci, USA vol. 87, pp. 3279–3283, May 1990 Medical Sicences, Isolation of Fetal DNA From Nucleated Erythrocytes in Maternal Blood, Diana W. Bianchi, Alan F. Fling, Mary Frances Pizzimenti, Joan H. M. Knoll, and Samuel A. Latt.

Human Glycogens, Glucose–6–Phosphatase of the Liver in Glycogen Storage Disease, Gerty T. Cori and Carl F. Cori, Jun. 27, 1952.

Liver Microsomal Glucose 6–Phosphatase, Inorganic Pyrophosphatase, and Pyrophosphate–Glucose Phosphotransferase, Robert C. Nordlie and William J. Arion, Sep. 30, 1964, vol. 240, No. 5, Journal of Biological Chemistry.

Am. J. Hum. Genet. 53:722–729, 1993, Cosegregation of Ingragenic Markers With a Novel Mutation That Causes Crigler–Najjar Syndrome Type 1: Implication in Carrier Detection and Prenatal Diagnosis, Nabil Moghrabi, Douglas J. Clark, Brian Burchell, and Maureen Boxer.

Blood, vol. 87, No. 2 (Jan. 15) 1996; p. 762–770, The Ontogeny of Key Endoplastic Reticulum Proteins in Human Embryonic and Fetal Red Blood Cells.

Am. J. Hum. Genet. 30:271–282, 1978, Prenatal Diagnosis of Hypophosphatasia: Genetic, Biochemical, and Clinical Studies, Richard A. Mulivor, Michael Mennuti, Elaine H. Zackai, and Harry Harris.

Early Human Development 42 (1995) 85–95, The Ontogeny of the Glucose–6–Phosphatase Enzyme in Human Embryonic and Fetal Red Blood Cells, Robert Hume, Sima Pazouki, Anne Hallas, and Ann Burchell.

Oxford University Press, Human Reproduction vol. 6, p. 1466–1468, Fetal Cells in the Maternal Circulation: Isolation by Multiparameter Flow Cytometry and Confirmation by Polymerase Chain Reaction.

Prenatal Diagnosis, vol. 11, 117–123 (1991), Detection of Fetal Blood Cells in Maternal Blood, S. C. Yeoh, I. L. Sargent, C. W. G. Redman, B. P. Wordsworth, and S. L. Thein.

The Lancet, 1990; vol. 336: 197–200, Isolation of Fetal Trophoblast Cells From Peripheral Blood of Pregnant Women, U. W. Mueller, C.S. Hawes, A. E. Weight, A. Petropoulos, E. Deboni, F. A. Firgaira, A. A. Morley, D. R. Turner, and W. R. Jones.

J. Med Genet 1993; 30: 1051–1056, Prenatal Diagnosis From Maternal Blood: Simultaneous Immunophenotyping and FISH of Fetal Nucleated Erythrocytes Isolated by Negative Magnetic Cell Sorting, Yun–ling Zheng, Nigel P. Carter, Cathy M. Price, Susan M. Colman, Peter J. Milton, Gerald A. Hackett, Melvyn F. Greaves, and Malcolm A. Ferguson–Smith.

Nature Genetics, vol. 14, Nov. 1996, Prenatal Diagnosis of Sickle Cell Anaemia and Thalassaemia by Analysis of Fetal Cells in Material Blood 264–268.

Histol Histopathol (1995) 10: 979–993, The Glucose–6–Phosphatase System in Human Development, A. Burchell and R. Hume.

Human Genetics 1993, 91: 427–43, (exact title cut–off) Nucleated Cells in Maternal Peripheral Blood: and Relationship to Gestational Age, Hamada, Tadao Arinami, Takeshi Kubo, Hideo Hamaguchi, and Hirokazu Iwassaki.

Hum. Genet (1992), 90:368–370, Detection of Fetal Cells With 47, XY, +21 Karyotype in Maternal Peripheral Blood, Diana W. Bianchi, Anna Mahr, Gretchen K. Zickwolf, Timothy W. Houseal, Alan F. Flint, and Katherine W. Klinger.

Journal of Reproductive Medicine, Fetal Cells in the Maternal Circulation, Wolfgang Holzgreve, Henk S. P. Garritsen, and Dorothee Ganshirt–Ahlert, p. 410–418.

Clinica Chimica Acta, 128 (1983) 271–281, Prenatal Diagnosis of Galactosemia and Properties of Galactose–1–Phosphate Uridyltransferase in Erythrocytes of Galactosemic Variants as well as in Human Fetal and Adult Organs, Yoon s. Shin, W. Endres, M. Rieth, and J. Schaub.

Molecular Membrane Biology, 1994, 11, 217–227, Glucose–6–Phosphatase Proteins of the Endoplastic Reticulum (Review), Ann Burchell, Bernard B. Allan, and Robert Hume.

Biology of Reproduction 55, 298–303 (1996), Human Fetal Testis Endoplastic Reticulum Glose–6–Phosphatase Enzyme Protein, Ann Burchell, Sharlene L. Watkins, and Robert Hume.

Journal of Clinical Endocrinology and Metabolism, vol. 80, No. 6, The Human Adrenal Microsomal Glucose–6–Phosphatase System, Robert Hume, Michael Voice, Sima Pazouki, Roberta Giunti, Angelo Benedetti, and Ann Burchell.

Biochem. J. (1985) 230, 489–495, Ann Burchell and Brian Burchell, Stabilization of Glucose–6–Phosphatase Activity by a 21 000–Dalton Hepatic Microsomal Protein.

Vol. 229, No. 1, 179–182, Ian D. Waddell, J. Gordon Lindsay, and Ann Burchell, Feb. 1988, The Identification of T2; the Phosphate Transport Protein of the Hepatic Microsomal Glucose–6–Phosphatase System.

The Journal of Biological Chemistry, vol. 263, No. 6, Issue of Feb. 25, pp. 2673–2678, 198, The Phosphohydrolase Component of the Hepatic Microsomal Glucose–6–Phosphatase System is a 36.5–Kilodalton Polypeptide, Janice L. Countaway, Ian D. Waddell, An Burchell, and William J. Arion.

The Lancet, May 9, 1987, p. 1059–1062, Diagnosis of Type 1a and Type 1c Glycogen Storage Diseases in Adults, Ann Burchell, Chim C. Lang, Roland T. Jung, William Bennett, and Alan N. Shepherd.

J. Inher. Metab. Dis. 12 Suppl. 2 (1989) 315–317, Perinatal Diagnosis of Type 1c Glycogen Storage Disease, A. Burchell, I. D. Waddell, L. Stewart, and R. Hume.

The Journal of Biological Chemistry, vol. 258, No. 16, Issue of Aug. 25, pp. 9739–9744, 1983, Type Ic, a Novel Glycogenosis, Robert C. Nordlie, Katherine A. Sukalski, Juan M. Munoz, and Jerry J. Baldwin.

Clinical Chemistry, 36, 1633 (1990), Ontogeny of Human Hepatic Microsomal Glucose–6–Phosphatase Proteins, Gibb. Waddell, Giles, and Hume.

Biochem J. (1992) 281, 859–863, Analysis of Human Hepatic Microsomal Glucose–6–Phosphatase in Clinical Conditions Where the T2 Pyrophosphate/Phosphate Transport Protein is Absent, Robert C. Nordlie, Hazel M. Scott, Ian D. Waddell, Ruber Hume, and Ann Burchell.

* cited by examiner

PRENATAL DIAGNOSTIC METHODS

This is a continuation of International Application PCT/GB98/00656, with an international filing date of Mar. 3, 1998. This application also claims priority from Provisional Application No. 60/067,520, filed Dec. 4, 1997, and Great Britain Application No. 9704876.3, filed Mar. 8, 1997.

The present invention relates to diagnostic methods, in particular to methods of prenatal diagnosis and to reagents for use in such methods.

Prenatal diagnosis is carried out widely in hospitals throughout the world. Existing procedures such as fetal, hepatic or chorionic biopsy for diagnosis of chromosomal disorders including Down's syndrome, as well as single gene defects including cystic fibrosis are very invasive and carry a not inconsiderable risk to the foetus and a small risk to the mother.

Amniocentesis, for example, involves a needle being inserted into the womb to collect cells from the embryonic tissue or fluid. The test, which can detect Down's syndrome, carries a miscarriage risk estimated at 1%.

Fetal therapy is in its very early stages and the possibility of very early tests for a wide range of disorders would undoubtedly greatly increase the pace of research in this area. Current fetal surgical techniques have improved, making fetal surgery for some genetic problems like spina bifida and cleft palate very feasible. In addition, relatively simple effective fetal treatment is currently available for other disorders for example 21-hydroxylase (treatment with dexamethasorie) and holocarboxylase synthetase (treatment with biotin) deficiencies, as long as detection can take place early enough.

Thus, relatively non-invasive methods of prenatal diagnosis are an attractive alternative to the very invasive existing procedures. A method based on maternal venepuncture should make earlier diagnosis more widely available in the first trimester, increasing options to parents and obstetricians (because genetic disorders could be detected earlier and more safely), and allowing the eventual development of specific fetal therapy.

The possibility of recovering fetal cells from the maternal circulation has excited general interest as a possible means, non-invasive to the fetus, of diagnosing fetal anomalies (Simpson & Elias (1993) *J. Am. Med. Assoc.* 270, 2357–2361). Initial interest was directed towards trophoblastic detection systems but separation of those cells by flow cytometry has been unreliable as maternal lymphocytes appeal to absorb proteins released by trophoblastic cells (Mueller et al (1990) Lancet 336, 197–200; Covone et al (1984) Lancet 13 October edition, 841–843). More recently, attention has focused on the development of methods to isolate fetal blood cells for cytogenetic analysis particularly nucleated fetal erythrocytes as their numbers exceed those of fetal lymphocytes in the maternal circulation. Identification of fetal red blood cells in maternal blood has been described ie in a male fetus with Y centromere probes to identify fetal cells or amplification of Y-specific DNA sequences (Price et al (1991) *Am. J. Obstet. Gynecol.* 165, 1731–1735; Zheng et al (1993) *J. Med. Genet.* 30, 1051–1056; Hamada et al (1993) *Hum. Genet.* 91, 427–432; Cheung et al (1996) *Nature Genetics* 14, 264–268; and Williamson (1996) *Nature Genetics* 14, 239–249) or karyotype identification in trisomic conditions (for example, see Bianchi et al (1992) *Hum. Genet.* 90, 368–370).

Hume et al (1995) *Early Human Development* 42, 85–95 shows that the microsomal glucose-6-phosphatase enzyme protein is present in human embryonic and fetal red blood cells.

Pazouki et al (1996) *Acta histochem.* (Jena) 98, 29–37 attempts to identify fetal nucleated red blood cells using combined immunocytochemistry using a human fetal haemoglobin antibody and an in situ hybridisation method using X and Y chromosome probes.

Hume et al (1996) *Blood* 87, 762–770 describes study of the expression of endoplasmic reticulum proteins in human embryonic and fetal red blood precursors.

Wachtel et al (1991) *Human Reproduction* 6, 1466–1469 describes the use of PCR to identify Y-specific DNA sequences in maternal cells isolated by cell sorting with transferrin receptor antibody and glycophorin A antibody.

Yeoh et al (1991) *Prenatal Diagnosis* 11, 117–123 describes the detection of fetal cells in the maternal circulation by enzymatic amplification of a single copy gene that was fetal specific.

Holzgreve et al (1992) *J. Reprod. Med.* 37, 410–418 shows that the transferrin receptor antigen alone is not sufficient for enrichmnent of fetal nucleated erythrocytes and points out that the reproducibility and reliability of the techniques are still limited, mainly due to the lack of very specific cell markers.

Zheng et al (1993) *J. Med. Genet.* 30, 1051–1056 describes the use of a magnetic activated cell sorter (MACS) to enrich fetal nucleated erythrocytes using mouse monoclonal antibodies specific for CD45 and CD32 to deplete leucocytes from maternal blood. The paper points out that significant maternal contamination was present even after MACS enrichment preventing the accurate analysis of fetal cells by interphase fluorescence in situ hybridisation (FISH).

Tomoda (1964) *Nature* 202, 910–911 describes the demonstration of fetal erythrocytes by immunofluorescent staining.

There exists a need for improved methods for identifying fetal cells in maternal blood in order to carry out prenatal diagnosis.

We attempted to isolate embryonic and fetal nucleated red blood cell from maternal blood with the established immuno-magnetic sorting using sequentially anti-CD45 and anti-CD18 antibodies to remove white blood cells and then anti-CD71 (transferrin receptor) antibodies to enrich fetal nucleated red blood cells. We were very disappointed to discover that immuno-magnetic sorting, with the anti-CD71 antibody, did not purify embryonic red blood cells of the megaloblastic series. The advantage of purifying megaloblastic cells is that they are the predominant red blood cell type in the embryo and early fetus and that they are nucleated whereas the vast majority of adult red blood cells are normocytic and non-nucleated.

In subsequent conventional immunohistochemistry, we found that CD71 interactions with megaloblasts were very weak presumably explaining the poor purification of embryonic cells with this antibody. This is a very major problem in the current use of maternal blood for early diagnosis. We have shown that the nucleated megaloblastic series predominates in early development compared to nucleated normoblasts. This means that using the conventional antibodies ie anti-CD71, it is very difficult to obtain pure nucleated haemopoeitic cells arising from the early conceptus. Anti-CD71 does not immunoreact with the majority of these early cells making this technique possible in specialised research labs with specialist staff and equipment, but not practical in routine service laboratories.

The use of anti-CD71 is described in Cheung et al (1996) *Nature Genetics* 14 264–268 and is reviewed by Williamson (1996) *Nature Genetics* 14, 239–240. Having to look at thousands of cells to find a few fetal ones on slides is a problem with this approach, as is the fact that anti-CD71 antibodies are not selective enough for fetal cells and do not react with embryonic cells.

An object of the present invention is the provision of improved methods for identifying fetal cells in, and isolating them from, maternal blood. In particular, an object of the invention is the provision of methods of identifying and isolating embryonic or early fetal red blood cells, and analysing the cells for fetal abnormalities.

A first aspect of the invention provides a method of identifying embryonic or fetal red blood cells in a sample containing natural blood cells and embryonic or fetal red blood cells or both, the method comprising determining which cell or cells contain or express an adult liver component.

A second aspect of the invention provides a method of isolating embryonic or fetal red blood cells from a sample containing maternal blood cells and embryonic or fetal red blood cells or both, the method comprising isolating the cells which contain or express an adult liver component.

It has not previously been proposed that embryonic or early fetal nucleated red blood cells are functioning as adult liver cells while circulating in the bloodstream.

Suitably, the sample containing maternal blood cells and embryonic or fetal red blood cells or both is a sample of blood from a pregnant female.

Preferably the fetal red blood cell is an early fetal red blood cell.

The pregnant female may be any mammal and in particular a mammal of commercial or agricultural importance or a domesticated mammal. Suitably, the mammal is a horse, cow, sheep, pig, goat, dog, cat or the like. The basic pattern of haematological development in the embryo and fetus is the same for all mammals.

Preferably the pregnant female is human.

A particular advantage of the present invention is that the methods identify, and can be used to isolate, embryonic and early fetal red blood cells at an early stage of gestation. Thus, it is preferred if the maternal blood sample is taken from the pregnant female at an early stage of pregnancy. In the case of a pregnant human female it is preferred if the sample is taken in the first trimester.

In general the earlier in pregnancy, whether for potential fetal therapy or the option of termination, the better (ideally less than 10 weeks gestation). A further practical reason is that the means of termination of pregnancy is technically easier at earlier gestations and with less physical and psychological side-effects. There is no upper limit for intrauterine diagnosis of fetal anomalles and even late in pregnancy treatment may still be beneficial in utero or the immediate newborn period. The ontogeny of nucleated embryonic and fetal cells clearly indicates that the percentage of those cells in the embryo/fetus is higher in the first trimester than later in pregnancy. However, the total fetal blood volume increases with gestation and proportionally fetal to maternal transfusion volumes may be greater.

The detailed structure of the developing human conceptus, sufficient for accurate dating in days, has only been described in detail up to 56 day post-ovulatory days and the descriptive term, embryo, will be used as the convention for this developmental staging procedure (O'Rahilly & Muller (1987) *Developmzental Stages in Human Embryos*, Publication 637, Washington: Carnegie Institute of Washington). The descriptive term, fetus, will be used for the remainder of human intrauterine development to term (>37 completed weeks gestation), with developmental age (to the nearest week) an estimate based on size, including crown-heel, crown-rump and heel-toe measurements and *Growth of the External Dimensions of the Human Body in the Fetal Period*, Minneapolis: University of Minnesota Press) menstrual history and ultrasound dating of pregnancy.

The methods of the invention are particularly suited to identify, and can be used to isolate, embryonic and fetal red blood cells of the nucleated megaloblastic series which predominate in early development compared to nucleated normoblasts. However, nucleated normoblasts may also be isolated or identified by the method with equal advantage. The proportion of megaloblasts are higher at earlier stages of pregnancy. The morphology of embryonic/early fetal megaloblast differs fundamentally from embryonic/fetal normoblasts and the small number of maternal normoblasts which could be present in the circulation. Maternal megaloblasts and megalocytes are extremely rare but do occur in vitamin B12 and a folate deficiency. For these reasons embryonic/early fetal megaloblasts are preferred but embryonic/early fetal normoblasts would also be capable of being used.

The sample containing maternal blood cells and embryonic or fetal red blood cells or both may be a sample from which has been removed certain maternal blood cells. For example, adult white blood cells can be removed from maternal blood using sequentially anti-CD45 and anti-CD18 antibodies although with a relatively poor efficiency. Enrichment of samples may be achieved by density centrifugation (eg Ficoll gradients) but will not separate adult and fetal nucleated cells.

The sample may be a sample which has been enriched for fetal cells. For example, it could be a sample enriched by the use of an anti-transferrin receptor antibody as described in Cheung et al (1996) *Nature Genetics* 14, 264–268.

The sample (particularly when it is one which fetal or embryonic cells are to be identified in rather than isolated from) may be one which has been treated in order to undertake haematological, biochemical, histochemical or molecular biological analysis or the like. For example, the sample may be a blood sample or a sample of a fraction of blood (such as one that has been enriched for fetal cells/depleted of maternal cells) which has been prepared for immunocytochemical analysis or for fluorescence in situ hybridisation (FISH) analysis or merely has been spread on a microscope slide.

The sample containing maternal blood cells and embryonic or fetal red blood cells or both may be any suitable sample (including a fluid) which contains such cells. For example, the sample may be urine from a patient with haematuria, amniotic fluid or fetal blood.

By "adult liver component" we mean a component of an adult liver cell which is predominantly associated with the adult liver and, if it is found at all in other tissues of the adult, it is either found at low levels in that other tissue compared to the liver or that the mass of the other tissue in which the said component is found, compared to the mass of the liver, is low so that the total amount of the adult liver component is higher in the whole liver compared to the total amount in the whole other tissue. When the adult liver component is found at low levels in that other tissue it is at least 10-fold higher in the liver, preferably at least 100-fold higher in the liver, compared to that other tissue. When the adult liver components is found at similar levels to the liver in other tissues, that other tissue has $\frac{1}{10}$ of the mass of the liver, more preferably $\frac{1}{25}$ of the mass of the liver.

While the kidney has many functions not related to liver, it can also carry out, to a lesser extent, some liver functions such as gluconeogenesis. It is particularly preferred if, in the above definition of adult liver component, the "other tissue" is not kidney.

For example, glucose-6-phosphatase is an adult liver component. Glucose-6-phosphatase levels in liver are much higher than glucose-6-phosphatase levels in total pancreas. However, glucose-6-phosphatase levels in islet cells (which are only a small proportion of cells in pancreas) can be as high as in liver. Similarly, GLUT2 is an adult liver component which is expressed in islet cells. Both are considered to be predominantly liver proteins in the sense that the total mass of islets in the human body is minute compared to the total mass of liver. The level of adult liver component is measured per unit cell fraction or per unit cell or per unit tissue.

The adult liver component is, therefore, typically, adult liver selective or adult liver specific.

The adult liver component may be any suitable such component and may include protein, RNA, carbohydrate entities and metabolites provided that these are predominantly associated with the adult liver and, if it is found at all in other tissues of the adult, it is either found at low levels in that other tissue compared to the liver or that the mass of the other tissue in which the component is found compared to the mass of the liver is low so that the total amount of the adult liver component is higher in the whole liver compared to the total amount in the whole other tissue.

The embryonic or fetal cells may be identified or isolated according to the methods of the invention by the detection of, or binding to, of one or more adult liver components as defined.

It is particularly preferred if the adult liver component is substantially to absent from maternal cells of the maternal blood. Preferably, compared to embryonic or fetal red blood cells, maternal cells of the maternal blood contain less than 1% of the adult liver component on a per cell basis; more preferably they contain less than 0.1% on a per cell basis.

It is possible, when the liver has been acutely damaged by trauma, cells or clumps could be disseminated in the bloodstream. Thus, it is preferred if the sample is not a sample of blood from a female whose liver has been damaged so as to release liver cells into the blood. It is also preferred that the sample is not any other sample that contains adult liver cells.

Liver damage is assessed by plasma estimation of routine liver function tests, eg alanine aminotransferase activity. Morphologically, the appearance of a circulating adult liver cell and an embryonic nucleated red blood cell are sufficiently distinct to allow discrimination.

Preferably, the adult liver component is a protein.

Preferably, the adult liver protein is any one of a microsomal glucose-6-phosphatase enzyme, another protein component of the glucose-6-phosphatase system including the phosphate or glucose or glucose-6-phosphate transporters, a uridine diphosphate-glucuronosyltransferase (UDPGT), a cytochrome P450 isozyme (P450), nicotinamide adenine dinucleotide phosphate (NADP) cytochrome P450 reductase (P450 reductase), glucose transporter 2 (GLUT2), a P-glycoprotein, a MDRP (multidrug resistance protein), a MRP (multidrug resistance-like protein), γ-glutamyl transpeptidase, a lipoprotein receptor, an alkaline phosphatase, a bile salt transporter, a bile acid transporter, a hormone receptor, a multiple organic ion transporter (MOAT; equivalent to MRP), a bilirubin transporter (bilitranstocase) or bilirubin conjugate (eg bilirubin glucuronide) transporter (equivalent to MRP).

The liver plasma membrane contains transporters for a wide variety of drugs, xenobiotics and endogenous compounds because they are taken up by the liver which is their major site of metabolism. Similarly, the conjugated metabolites are then exported back out across the liver plasma membrane. The transporters, many of which are adult liver components as defined, are suitable targets for the practice of the methods of the invention. It will be appreciated that further transporters of this type will be purified and their corresponding cDNAs and genes cloned. The invention contemplates that the further, as yet unknown transporters, will be suitable targets.

In the case where there are isozymes of a particular protein or class of proteins which are not adult liver selective or adult liver specific, it is the adult liver selective or adult liver specific isozymes which are used. For example, certain P450s are not adult liver selective or adult liver specific and so, in the practice of the invention, it is those P450s which are adult liver selective or adult liver specific which are relevant. Typically, xenobiotic-metabolising P450s are liver-selective or liver specific.

Suitably, particularly when the said embryonic or fetal red blood cells are to be isolated from the sample, the adult liver component is a cell surface component. It will, nevertheless, be appreciated that the said cell surface components are useful for both isolation and identification purposes, and cell surface components are preferred for both isolation and identification purposes.

Preferably, the cell surface component is a plasma membrane protein which is predominantly associated with the adult liver plasma membrane and, if it is found at all in other tissues of the adult, it is found at low levels.

Conveniently, the adult liver plasma membrane protein is any of GLUT2, a P-glycoprotein, a MDRP, a MRP, γ-glutamyl transpeptidase, a lipoprotein receptor, an alkaline phosphatase, a bile salt transporter, a bile acid transporter, a hormone receptor, a MOAT, a bilirubin transporter or a bilirubin conjugate transporter, all as defined above.

If the transferrin receptor is an adult liver component as defined, preferably the adult liver component is not transferrin receptor.

In order to identify or isolate the embryonic or fetal red blood cell it is preferred if said sample is contacted with a binding moiety which bindings moiety binds to said adult liver component and said embryonic or fetal cell is identified in, or isolated from, the sample by virtue of being bound to the binding moiety.

It will be appreciated that the embryonic or fetal red blood cells may be identified in other ways.

For example, many of the adult liver components are enzymes and so the cells can be identified by the presence of the enzyme. Suitably, histochemical stains for glucose-6-phosphatase may be used. Also suitably assays for UDP glucuronosyltransferase are useful.

The invention also contemplates identifying the cells by detecting adult liver components which are mRNAs by using, for example, reverse transcriptase polymerase chain reaction (RT-PCR).

In a further preferred embodiment the adult liver component is detected intracellularly. For example, when the adult liver component is an enzyme, it is convenient to use a substrate (which enters the cell which cell may or may not be permeabilised depending on the substrate) and which, when metabolised by the said enzyme, gives a fluorescent or coloured product or a product which can readily be identified. It will be appreciated that in this embodiment the embryonic or early fetal red blood cells will be fluorescent or coloured (or marked in some other way) by virtue of the presence of the said product produced by the said enzyme. Fluorescent cells can be separated from non-fluorescent cells using a FACS sorter. Substrates for glucose-6-phosphatase which give rise to a coloured product are known in the art.

In addition to individual established protein components of adult liver, as potential sources of antibodies for embryonic and fetal cell isolation and/or identification, the following approach is also useful. Human and/or other mammalian liver plasma membranes are isolated by differential centrifugation from homogenised liver (or by other techniques known in the art) and either (a) directly used to raise antibodies or (b) subfractionation of liver plasma membranes is carried out prior to raising antibodies against particular components. Such antibodies will be polyspecific polyclonal antibodies which bind to the adult liver plasma membrane and, according to the invention, to the plasma membrane of embryonic and fetal red blood cells.

It will be appreciated that mixtures of defined antibodies directed at adult liver plasma membrane components are also usefull in the methods of the invention.

Preferably, the antibodies bind to portions of the adult liver plasma membrane components which are exposed on the surface of the cell.

Conveniently, the said binding moiety is an antibody or fragment or derivative thereof.

Monoclonal antibodies which will bind to many of these antigens (whether protein antigens or non-protein antigens) are already known but in any case, with today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "*Monoclonal Antibodies: A manual of techniques*", H Zola (CRC Press, 1988) and in "*Monoclonal Hybridoma Antibodies: Techniques and Applications*", J G R Hurrell (CRC Press, 1982).

Chimaeric antibodies are discussed by Neuberger et al (1988, 8*th International Biotechnology Symposium* Part 2, 792–799).

Polyclonal antibodies are useful in the methods of the invention.

Monospecific polyclonal antibodies are preferred. Suitable polyclonal antibodies can be prepared using methods well known in the art.

Fragments of antibodies, such as Fab and $Fab_2$ fragments may also be used as can genetically engineered antibodies and antibody fragments.

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sci. USA 81, 6851–6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) Science 242, 423; Huston et al (1988) *Proc. Natl. Acad. Sci. USA* 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293–299.

By "ScFv molecules" we mean molecules wherein the $V_H$ and $V_L$ partner domains are linked via a flexible oligopeptide.

Fab, Fv, ScFv and dAb antibody fragments can all be expressed in and secreted from *E. coli*, thus allowing the facile production of large amounts of the said fragments.

Whole antibodies, and $F(ab')_2$ fragments are "bivalent". By "bivalent" we mean that the said antibodies and $F(ab')_2$ fragments have two antigen combing sites. In contrast, Fab, Fv, ScFv and dAb fragments are monovalent, having only one antigen combining sites.

It will be appreciated that when the adult liver component is a receptor the receptor, and hence the embryonic or fetal red blood cell can be identified using a ligand for the receptor. For example, the cognate hormone is a ligand for a hormone receptor.

Typically, in a method of identifying the embryonic or fetal red blood cells, the binding moiety is detectably labelled or, at least, capable of detection. For example, the binding moiety is labelled with a radioactive atom or a coloured molecule or a fluorescent molecule or a molecule which can be readily detected in any other way. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Typically, in a method of isolating the embryonic or fetal red blood cells, the binding moiety is immobilised on a solid support so that the embryonic or early fetal red blood cells can be isolated by affinity binding. Conveniently, die solid support comprises any suitable matrix such as agarose, acrylamide, Sepharose (a trademark) and Sephadex (a trademark). The solid support may also be a solid substrate such as a microtitre plate or the like.

Advantageously, the binding moiety is magnetically labelled (either directly or indirectly) such that, when bound, the embryonic or fetal cell can be separated from the rest of the sample upon provision of a suitable magnetic field. Microbeads used for magnetic cell sorting are often termed MACS colloidal super paramagnetic microbeads.

Fetal or embryonic cells labelled in this way may be sorted by magnetic activated cell sorting (MACS).

Suitably, the binding moiety is labelled with a fluorescent molecule (either directly or indirectly) and the embryonic or fetal red blood cells are isolated using a fluorescence activated cell sorter (FACS).

We have, therefore, developed tools and methods which clearly identify, and show you that you are looking at, the correct cell type (ie embryonic or fetal red blood cells).

A third aspect of the invention provides a method of determining a fetal abnormality the method comprising identifying or isolating embryonic or fetal cells according to the method of the first or second aspects of the invention and analysing said embryonic or fetal cell for said fetal abnormality.

In one embodiment, cells are identified using a binding moiety, or identified by virtue of the presence of a said enzyme, as described above and the analysis of the said fetal abnormality is carried out directly on the identified cells. For example, cells can be identified immunohistochemically using a suitable binding moiety, or using a suitable enzyme-detection system, and the analysis of the fetal abnormality is carried out in situ on the so identified cell using techniques such as fluorescent in situ hybridisation (FISH) to detect chromosomal abnormalities. The polymerase chain reaction may be used in situ. While fluorescent detection systems work well, it is also possible to use labelled probes and enzyme-linked detection systems.

In a particularly preferred embodiment the embryonic or fetal cells are isolated according to the second aspect of the invention. The cells isolated by this procedure are substantially all embryonic or fetal cells and, in particular, there are substantially no maternal cells present.

Analysis of fetal abnormality involves analysis of the said embryonic or fetal cells according to what potential abnormality is to be investigated.

Although the method can be used according to the invention, it is preferred that a familial defect in glucose-6-phosphatase is not detected, or that disorders of liver protein expression are not diagnosed when the cells are identified by using a binding moiety which binds to an intracellular adult liver component such as glucose-6-phosphatase.

Although the method can be used according to the invention, it is also preferred that a genetic deficiency of an endoplasmic reticulum protein is not detected when the cells are identified using a binding moiety which binds to an intracellular adult liver component.

It is preferred if the fetal cell abnormality is determined by analysing the genetic material. In particular, the genomic DNA make up of the fetal cells isolated by the method of the second aspect of the invention will be the same as the genetic DNA make up of the somatic cells of the fetus. In one preferred embodiment chromosomal abnormalities are detected. By "chromosomal abnormality" we include any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome which can be detected by DNA analysis. The following table indicates certain genes, mutations in which lead to particular genetic diseases.

| Disease | Defective gene |
| --- | --- |
| Immunodeficiency | Adenosine deaminase |
|  | Purine nucleoside phosphorylase |
| Hypercholesterolaemia | LDL receptor |
| Haemophilia | Factor IX |
|  | Factor VIII |
| Gaucher's disease | Glucocerebrosidase |
| Mucopolysaccharidosis | β-glucuronidase |
| Emphysema | α1-antitrypsin |
| Cystic fibrosis | Cystic fibrosis transmembrane regulator |
| Phenylketonuria | Phenylalanine hydroxylase |
| Hyperammonaemia | Ornithine transcarbamylase |
| Citrullinaemia | Arginosuccinate synthetase |

-continued

| Disease | Defective gene |
| --- | --- |
| Muscular dystrophy | Dystrophin |
| Thalassaemia | β-globin |
| Sickle cell anaemia | β-globin |
| Leukocyte adhesion deficiency | CD-18 |

Other genetic disorders which can be detected by DNA analysis are known such as 21-hydroxylase deficiency or holocarboxylase synthetase deficiency, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranchiing enzyme deficiency (Type III glycogen storage disease). These and other genetic diseases are mentioned in *The Metabolic and Molecular Basis of Inherited Disease,* 7th Edition, Volumes I, II and III, Scriver, C. R., Beaudet, A. L., Sly, W. S., and Valle, D. (eds), McGraw Hill, 1995. Clearly, any genetic disease where the gene has been cloned and mutations detected can be analysed by this embodiment of the method of the invention.

Genetic assay methods include the standard techniques of restriction fragment length polymorphism assays and PCR-based assays, as well as other methods described below.

The assay may involve any suitable method for identifying mutations or polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, ie capable of detecting a mutation at another position or gene which is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

Amplification of DNA may be achieved by the established PCR method as disclosed by Saiki et al (1988) *Science* 239, 487–491 or by developments thereof or alternatives such as the ligase chain reaction, QB replicase and nucleic acid sequence-based amplification.

An "appropriate restriction enzyme" is one which will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence which occurs only rarely.

In another method, a pair of PCR pris are used which match (ie hybridise to) either the wild-type genotype or the mutant genotype but not both. Whether amplified DNA is produced will then indicate the wild-type or mutant genotype (and hence phenotype). However, this method relies partly on a negative result (ie the absence of amplified DNA) which could be due to a technical failure. It is therefore less reliable and/or requires additional control experiments.

A preferable method employs similar PCR pris but, as well as hybridising to only one of the wild-type or mutant sequences, they introduce a restriction site which is not otherwise there in either the wild-type or mutant sequences.

In order to facilitate subsequent cloning of amplified sequences, primers may have restriction enzyme sites appended to their 5' ends. Thus, all nucleotides of the primers are derived from the gene sequence of interest or sequences adjacent to that gene except the few nucleotides necessary to form a restriction enzyme site. Such enzymes and sites are well known in the art. The primers themselves can be synthesized using techniques which are well known in the art. Generally, the primers can be made using synthesizing machines which are commercially available.

A fourth aspect of the invention provides a kit of parts for determining a fetal abnormality comprising (a) means for determining whether a cell contains or expresses an adult liver component and (b) means for analysing a cell for an abnormality.

The means for determining whether a cell contains or expresses an adult liver component includes the aforementioned binding moieties and reagents (eg substrates) for detecting the said enzymes when the adult liver component is an enzyme and reagents such as PCR primers, deoxynucleotides and a DNA polyase for detecting the said mRNA when the adult liver component is an mRNA. Antibodies, or fragments or derivatives thereof, to the adult liver components are preferred. It is particularly preferred if the adult liver component is a cell surface component as described above.

The means for analysing a cell for an abnormality include any such means. It is particularly preferred if the means are means for detecting a genetic abnormality. Suitable such means therefore includes nucleic acid molecules, such as PCR primers and probes, which selectively hybridise to a gene of interest, ie one in which a genetic abnormality is being sought.

A further aspect of the invention provides the use of a binding moiety which binding moiety binds to an adult liver component in a method of determining a fetal abnormality the method comprising identifying or isolating embryonic or fetal cells according to the method of the first or second aspect of the invention and analysing said embryonic or fetal cell for said fetal abnormality.

Preferably, the binding moiety is used in a method where the fetal cell abnormality is determined by analysing genetic material, for example for chromosomal abnormalities or mutations in DNA.

A still further aspect of the invention provides the use of a means for determining whether a cell contains or expresses an adult liver component for identifying or isolating an embryonic or fetal red blood cell.

The means for determining whether a cell contains or expresses an adult liver component are those as described in the fourth aspect of the invention.

The invention will now be described in more detail with reference to the following Examples and Figure wherein:

FIG. 1 (95chorion aGLUT2 1;100X40RH) shows a human chorionic villus at 56 post-ovulatory days showing intense alpha GLUT 2 immunoreactivity in a megaloblast (arrow) and no reactivity in a normocyte (arrowhead) within a fetal chorionic blood vessel (bv). The syncytiotrophoblastic (s) and cytotrophoblastic (c) layers are minimally immunoreactive.

EXAMPLE 1

Antibodies Directed at Adult Liver Components

Antibodies directed against purified rat liver testosterone/4-nitrophenol UDPGT are raised in Suffolk Cross Blackface sheep by a combination of intradermal and subcutaneous injection. IgG is prepared from the antiserum by a combination of ammonium sulphate precipitation and diethyl aminoethyl-cellulose chromatography (Burchell et al (1984) *Biochem. Soc. Trans.* 12, 50). Typically sheep antirat liver testosterone/4-nitrophenol UDPGT antibody preparation (RAL 1) inhibit UDPGT activity towards bilirubin, testosterone, 1-naphthol, and rosterone, estrone, and morphine, and immunoblotting confirms a broad spectrum of cross-reactivity to multiple isoforms in rat and human adult and fetal liver microsomes.

Monospecific polyclonal antisera to the catalytic subunit of the microsomal glucose-6-phosphate system, T2, and T3 are each raised in Cheviot sheep by 3 subcutaneous injections of 80 $\mu$g of purified protein and Freund's complete adjuvant as described (Burchell & Waddell: Genetic deficiencies of the hepatic microsomal glucose-6-phosphatase system, in Randle et al (eds): Genetics and Human Nutrition, London, UK, Libbey, 1990, p93; Waddell et al (1991) *Bioclem. J.* 275, 363; Burchell & Cain (1985) Diabetologia 28, 852). Preimmune serum is obtained from each sheep before injection with antigen. The glucose-6-phosphatase enzyme, T2, and T3 used as antigens are all isolated from starved Wistar rat hepatic microsomes. Antisera are further purified by $(NH_4)_2SO_4$ fractionation and affinity purification using protein G columns. The antibody preparations, although raised against rat liver proteins, have been shown many times to each cross-react well with the respective human proteins as judged by immunoblot analysis after sodium dodecyl sulfate-polyacrylamide gel electrophoresis.

Antisera are raised in rabbits to methyl-moximated PGEM (PGEM-MOX) coupled to bovine serum albumin (Kelly et al (1986) *Prostaglandins Lelukot. Med.* 24, 1). In radioimmuno-assay, the PGEM-MOX antiserum has only a 0.05% cross-reactivity with $PGE_2$. Cross-reactions of PGEM-MOX antiserum to other methyl-moximated PGs are typically less than 0.02%, except for 15-keto-$PGE_2$ (12%) and 15-keto-$PGE_{2\alpha}$ (0.9%). The percentage cross-reactivities of PGEM-MOX antiserum to other PGs are typically less than 0.02%, except for 6,15-diketo-13,14-dfliydro-$PGE_{2\alpha}$ (0.35%); 13,14-dihydro-$PGE_{2\alpha}$ (2%); and 15-keto-$PGF_{2\alpha}$ (4%). Cross-reactivity of Gemeprost to PGEM-MOX antiserum is typically less than 0.03% and to PGFM-MOX antiserum, 0.03%. Antibody specificity of PGEM-MOX antiserum for immunohistochemistry is shown by selective absorption of immunostaining by PGEM-MOX (Hume et al (1993) *Exp. Lung Res.* 19, 361). Anti-PGHS-1, a polyclonal goat IgG fraction with cross-reactivity to PGHS-1 from a number of mammalian species but negligible reactivity to PGHS-2, and a monoclonal 15-hydroxyprostaglandin dehydrogenase antibody are purchased from Oxford Biomedical Research, Inc (Oxford, Mich.).

$PGE_2$ is conjugated to keyhole limpet hemocyanin and injected intradermally into sheep. The resultant $PGE_2$-antiserum, on radioimmunoassay, is highly group-selective, with minimal cross-reactivity between the F and E series of PGs. Cross-reactivity of Gemeprost to $PGF_2$-antiserum is typically less than 1%. Antisera specificity for immunohistochermistry is tested by selectivity of absorption of immunostaining by $PGE_2$ in human fetal lung (Hume et al (1992) *Exp. Lung Res.* 18, 259).

Antibodies to purified cytoctirome P450s are isolated as described in Wolf et al (1984) *Carcinogenesis* 5, 993. The isozyme specificities of the antisera made in this way have been shown by immunoblot analysis with expressed human recombinant cytochrome P450 proteins (Forrester et al (1992) *Biochem. J.* 281, 359). NADPH-cytochrome P450 oxidoreductase is purified (Wolf et at (1984) *Carcinogenesis* 5, 993) and antibodies raised in rabbits are shown to cross-react with the human enzyme on sodium dodecyl sulfate-polyacrylamide gel electrophoresis (Smith et al (1994) *Proc. Natl. Acad. Sci. USA* 91, 8710).

In addition to antibodies made using isolated proteins as an antigen, antipeptide antibodies are also useful.

Antipeptide antibodies are synthesised on the basis of known sequence information and/or larger portions of proteins which have been generated using portions of the cDNA or gene linked to appropriate sequences which facilitate isolation after overexpression in a suitable system, eg bacteria. A series of antipeptide antibodies against portions of the human glucose-6-phosphatase enzyme (CSHIHSIYNASLKKY (SEQ ID No: 1); CMNVLHDF-GIQSTHY (SEQ ID No: 2); CLAQVLGQPHKKSL (SEQ ID No: 3); and CLSRIYLAAHFPHQ (SEQ ID No: 4)) have been made as follows.

These peptides were conjugated to keyhole limpet hemocyanin and injected into sheep by intradermal and subcutaneous routes. The resultant antipeptide antiserum have been shown to cross react and can be used for immunohistochemical detection of glucose-6-phosphatase containing cells including fetal and embryonic cells.

EXAMPLE 2

Combined Immunocytochemical and Fluorescence In Situ Hybridisation Analysis of a Maternal Blood Sample to Detect Trisomy 21

Blood samples and cell preparation. Peripheral venous blood samples (EDTA) are obtained from a pregnant female in the first trimester. Five ml aliquots of blood are carefully layered over 3.5 ml aliquots of Polymorphoprep (Nycomed, Norway) in 15 ml tubes which are then spun at 500 g for 30 min at room temperature. Mononuclear cells at the plasma/Polymorphoprep interface (upper of the two bands obtained) are harvested using a Pasteur pipette and dispensed into a clean tube. The cells are washed three times using 5 ml of cold phosphate buffered saline (PBS) containing 0.5% bovine serum albumin (BSA) and 5 mM ethylenediaminetetra-acetic acid (EDTA) followed by a 10 min spin at 400 g each time. The cell pellets are finally resuspended in PBS/BSA/EDTA at a concentration of $10^6$ cells/ml.

Slide preparation. Aliquots (100 μl) of blood mononuclear cells are cytocentrifuged onto glass slides (Cytospin, Shandon) and air dried overnight.

Immunocytochemistry. The following polyclonal and monoclonal antibodies are used in the immunocytochemical procedure: (a) a mouse monoclonal antibody directed to glucose-6-phosphatase enzyme (b) rabbit anti-mouse IgG (DANK) at 1:25, and (c) mouse PAP (DAKO) at 1:100. All antibodies are diluted in TBS containing 20% normal rabbit serum (Serotec) and antibody incubations are carried out in a humidified chamber at room temperature.

Dry cytospins are fixed in acetone for 3 min and washed for 5 min in two changes of Tris-buffered saline (TBS). The standard PAP technique (Sternberger et al, 1970, *J. Histochem. Cytochem.* 18, 315–333) is modified. Briefly, endogenous peroxidase activity is blocked using 0.3% hydrogen peroxide in TBS for 30 min after which time slides are rinsed in two changes of TBS for 5 min. Cytospins are incubated with 20% normal rabbit serum in TBS for 5 min to block non-specific binding sites. After removal of most of the normal rabbit serum. cytospins are incubated with anti-G6Pase monoclonal antibody for 30 min. After washing the slides in TBS as before, followed by incubation with 20% normal rabbit serum in TBS for 5 min, cytospins are incubated with rabbit anti-mouse IgG for 30 min. The slides are washed as above and incubated with 20% normal rabbit serum in TBS for 5 min followed by mouse PAP for 30 min. The slides are then washed as above and two to three drops of 3,3-diaminobenzidine (DAB) substrate solution are added and incubated at room temperature for 7 min. The DAB solution is prepared by dissolving 2.5 mg of DAB (Sigma) in 5 ml of TBS followed by the addition 0.1 ml of freshly prepared 1% hydrogen peroxide immediately before use. The slides are washed in running tap water for 2 min followed by a 5 min incubation in copper sulphate solution (0.4 g copper sulphate, 0.72 g sodium chloride, 100 ml distilled water) and rinsed again in running tap water. In order to check the morphology of the cells after immunocytochemistry, the slides may be counterstained with Mayer's hematoxylin (Sigma) for 20 min, dehydrated through graded alcohols, and checked using a light microscope Zeiss Axioskop 20.

Immunohistochemistry on tissue sections is performed using anti-G6Pase monoclonal antibody and a standard PAP technique (Sternberger et al, 1970, *J. Histochem. Cytochem.* 18, 315–333). Sections are lightly counterstained with haemotoxlyin, dehydrated through graded alcohol and cleared in xylene prior to coverslipping in synthetic resin.

Fluorescence in situ hybridisation (FISH). Following immunocytochemistry, cytospins are fixed in 3:1 (v/v) methanol:glacial acetic acid for 30 min at room temperature. The fixation is repeated with a fresh preparation of the same fixative for a further 30 min and with 70:30 (v/v) glacial acetic acid:water for 90 sec. The slides are washed for 5 min in two changes of PBS and then dehydrated through 70%, 85%, and 100% alcohol and air-dried at room temperature. FISH is performed using probes specific for human for human chromosome 21 directly labelled with fluorescein-isothiocyanate (FITC). Briefly, hybridisation fluid is pipetted onto each cytospin and a coverslip coated with the fluorescent probes is placed on top and sealed with rubber solution. In the presence of hybridisation fluid, the probes are eluted from the coverslip and after denaturation of both probe and target DNA which occurred under the coverslip by heating the slides to 70° C., the probes are allowed to hybridise to the targets for 25 min at 37° C. After several post hybridisation washes the slides are mounted in antifade solution containing diamidino-2-phenyl-indole dihyrochloride (DAPI).

Microscopy. Slides are analysed using a Zeiss Axioskop 20 microscope equipped with a microscope illuminator with cury vapour short-arc lamp HBO 50W and appropriate Zeiss filter combinations (02 for DAPI; 09 for FITC). The immiunopositive cells are located using the microscope in the visible light mode, after which the visible light source is blocked and the microscope switched to fluorescence mode and slides analysed using each filter set. Cells are photographed on Fujichrome Provia 400 colour film (Fuji Photo Film Co., Tokyo, Japan) both in visible light mode and fluorescence mode. Black and white negatives and prints are then made from the colour film.

Results

Three positive fluorescent spots from chromosome 21 are present in embryonic or fetal cells derived from an affected fetus. In contrast, normal maternal cells and normal fetal cells give two positive fluorescent spots for chromosome 21. Fetal and maternal cells are distinguished by immunoreactivity to glucose-6-phosphatase, ie fetal red blood cells are immunopositive, maternal red blood cells immunonegative.

EXAMPLE 3

Isolation of Fetal Cells and PCR Analysis for Sickle Cell Anaemia and Thalassaemia FIG. 1 (95chorion aGLUT2 1;100X40RH) shows a human chorionic villus at 56 post-ovulatory days showing intense alpha GLUT 2 immunoreactivity in a megaloblast (arrow) and no reactivity in a normocyte (arrowhead) within a fetal chorionic blood vessel (bv). The syncytiotrophoblastic (s) and cytotrophoblastic (c) layers are minimally immunoreactive.

Fetal cells from maternal blood taken in the first trimester are isolated in the following way, and a PCR analysis for Sickle cell anaemia and thalassaemia undertaken.

Blood sample and cell separation. Peripheral blood (16–18 ml) from pregnant women in the first trimester is collected into EDTA Vacutainer tubes (Becton Dickinson, Rutherford, N.J.). The blood is then diluted 1:2 with phosphate buffered saline (PBS), with each 15 ml layered over 10 ml Ficoll-paque plus (density 1.077 g/ml, Pharmacia Biotech, Piscatawa, N.J.) and centrifuged at 400 g for 30 min at room temperature. The interphase cells are then carefully removed, washed twice with PBS supplemented with 5 mM EDTA and 0.5% bovine serum albumin (BSA), and resuspended in 80 $\mu$l PBS/EDTA/BSA per each $10^7$ cells.

Magnetic activated cell sorting. Nucleated red cells were enriched by MiniMACS (Miltenyi Biotech, Inc., Sunnyvale, Calif.) following the manufacturer's protocol. An anti-GLUT2 antibody conjugated MACS Microbeads is added to the resuspended cells at the ratio of 20 $\mu$l per each $10^2$ cells. The mixture is then incubated for 15 min at 6–12° C. in a refrigerator. The magnetic-bead labelled cell suspension is pipetted on top of a MiniMACS column and the unlabelled cells are then collected by pushing them out of the column using 1 ml buffer and a plunger.

The cells isolated in this way are substantially all early fetal or embryonic nucleated red blood cells.

PCR is performed as described (Saiki et al (1988) Science 239, 487–491) in 50 $\mu$l reaction volume using a Perkin-El DNA Thermal Cycler. Each amplification cycle consists of 1 min at 95° C., 1 min at 55° C., and 1 min at 72° C., with 10 min final extension at 72° C. in the last cycle. DNA from the fetal or embryonic cells eluted from the MiniMACS column are first amplified for 40 cycles and a fifth of the products is examined on an 8% acrylamide gel. If no specific or very weak PCR products are seen, an aliquot of 10 $\mu$l of the first round PCR products is amplified for another 20–30 cycles using the same conditions. The primers used to amplify the β-globin sequences are biotinated 'pco3' (5'-Biotin-ACACAACTCTGTTCACTAGC-3' (SEQ ID No: 5)), biotinated 'β110' (5'-Biotin-AAAATAGACCAATAGGCAGA-3' (SEQ ID No: 6)) and biotinated 'China 2' (5'-Biotin-TGCAGCTTGTCACAGTGCAGCTCACT-3' (SEQ ID No: 7)). The 248-bp DNA amplified by 'pco3' and 'β110' is used for sickle gene detection. The 460-bp DNA amplified by 'pco3' and 'China 2' is used for β-thalassemia detection.

Reverse dot blot hybridization. Membrane strips containing multiple dots of immobilized normal and mutant oligonucleotide probes of β-globin sequences are prepared as described (Maggio et al (1993) *Blood* 81, 239–242; Cai et al (1994) *Human Mutation* 3, 59–63). The sequences of these oligonucleotide probes for detecting mutations are as follows: for detecting the sickle gene, the normal probe is 5'-TGACTCCTGAGGAGAAGT-3' (SEQ ID No: 8) and the mutant probe is 5'-CAGACTTCTCCACAGGA-3' (SEQ ID No: 9); for detecting the β39 mutation, the normal probe is 5'-CTTGGACCCAGAGGTTCTT-3' (SEQ ID No: 10) and the mutant probe is 5'-AGAACCTCTAGGTCCAAGG-3' (SEQ ID No: 11); and for detecting the β110 mutation, the normal probe is 5'-GAAAATAGACCAATAGGCAGA-3' (SEQ ID No: 12), and the mutant probe is 5'-CTGCCTATTAGTCTATTTTC-3' (SEQ ID No: 13). The PCR products of the fetal cells are added to a 0.8 ml solution containing 2×SSC/0.1% SDS. Strips containing the oligonucleotide probes are added and DNAs are denatured by boiling in a water bath for 5 min. Hybridization is carried out in a 42° C. water bath overnight. The strips are then washed in 0.5×SSC/0.1% SDS at 42° C. for 10 min, conjugated with streptavidin-HRP at room temperature for 15 min, and the colour developed with chromogenic substrate containing tetramethyl benzidine solution, Na citrate and $H_2O_2$ at room temperature until colours were visible whether or not the fetal cells have a sickle cell or thalassaemia mutation can be detected by this method.

What is claimed is:

1. A method of isolating embryonic or fetal red blood cells from a sample containing maternal red blood cells and embryonic or fetal red blood cells, the method comprising isolating the cells that contain or express glucose transporter 2 (GLUT2), the method comprising the steps of:

(a) contacting the sample with an anti-GLUT2 antibody that specifically binds the glucose transporter 2;
(b) allowing the anti-GLUT2 antibody to bind to the glucose transporter 2; and
(c) isolating the embryonic or fetal red blood cells by virtue of being bound to the anti-GLUT2 antibody.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Cys Ser His Ile His Ser Ile Tyr Asn Ala Ser Leu Lys Lys Tyr
 1               5                  10                  15

(2) INFORMATION FOR SEQ ID NO: 2:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 2:

Cys Met Asn Val Leu His Asp Phe Gly Ile Gln Ser Thr His Tyr
 1               5                  10                  15

(2) INFORMATION FOR SEQ ID NO: 3:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 3:

Cys Leu Ala Gln Val Leu Gly Gln Pro His Lys Lys Ser Leu
 1               5                  10

(2) INFORMATION FOR SEQ ID NO: 4:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 4:

Cys Leu Ser Arg Ile Tyr Leu Ala Ala His Phe Pro His Gln
 1               5                  10

(2) INFORMATION FOR SEQ ID NO: 5:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 5:

Ala Cys Ala Cys Ala Ala Cys Thr Gly Thr Gly Thr Thr Cys Ala Cys
 1               5                  10                  15
Thr Ala Gly Cys
            20

(2) INFORMATION FOR SEQ ID NO: 6:

(i) SEQUENCE CHARACTERISTICS:

(A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

Ala Ala Ala Ala Thr Ala Gly Ala Cys Cys Ala Ala Thr Ala Gly Gly
 1               5                  10                  15

Cys Ala Gly Ala
         20

(2) INFORMATION FOR SEQ ID NO: 7:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

Thr Gly Cys Ala Gly Cys Thr Thr Gly Thr Cys Ala Cys Ala Gly Thr
 1               5                  10                  15

Gly Cys Ala Gly Cys Thr Cys Ala Cys Thr
         20                  25

(2) INFORMATION FOR SEQ ID NO: 8:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

Thr Gly Ala Cys Thr Cys Cys Thr Gly Ala Gly Gly Ala Gly Ala Ala
 1               5                  10                  15

Gly Thr (2) INFORMATION FOR SEQ ID NO: 9:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Cys Ala Gly Ala Cys Thr Thr Cys Thr Cys Cys Ala Cys Ala Gly Gly
 1               5                  10                  15

Ala (2) INFORMATION FOR SEQ ID NO: 10:

(i) SEQUENCE CHARACTERISTICS:
        (A) LENGTH: 19 amino acids
        (B) TYPE: amino acid
        (C) STRANDEDNESS: single
        (D) TOPOLOGY: linear -continued (ii) MOLECULE TYPE: peptide (xi) SEQUENCE DESCRIPTION: SEQ ID NO: 10:

Cys Thr Thr Gly Gly Ala Cys Cys Ala Gly Ala Gly Gly Thr Thr
 1               5                  10                  15

Cys Thr Thr (2) INFORMATION FOR SEQ ID NO: 11:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Ala Gly Ala Ala Cys Cys Thr Cys Thr Ala Gly Gly Thr Cys Cys Ala
 1               5                  10                  15

Ala Gly Gly (2) INFORMATION FOR SEQ ID NO: 12:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Gly Ala Ala Ala Ala Thr Ala Gly Ala Cys Cys Ala Ala Thr Ala Gly
 1               5                  10                  15

Gly Cys Ala Gly Ala
             20

(2) INFORMATION FOR SEQ ID NO: 13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Cys Thr Gly Cys Cys Thr Ala Thr Thr Ala Gly Thr Cys Thr Ala Thr
 1               5                  10                  15

Thr Thr Thr Cys
         20